(12) United States Patent
Clark

(10) Patent No.: US 6,758,677 B2
(45) Date of Patent: Jul. 6, 2004

(54) APPARATUS AND METHOD FOR MONITORING THE VALIDITY OF A MOLECULAR MODEL

(75) Inventor: John D. Clark, Oceanside, CA (US)

(73) Assignee: Accelrys, Inc., San Diego, CA (US)

( * ) Notice: Subject to any disclaimer, the term of this patent is extended or adjusted under 35 U.S.C. 154(b) by 0 days.

(21) Appl. No.: 10/428,873

(22) Filed: May 2, 2003

(65) Prior Publication Data

US 2003/0194687 A1 Oct. 16, 2003

Related U.S. Application Data

(63) Continuation of application No. 09/312,234, filed on May 14, 1999, now Pat. No. 6,582,233.

(51) Int. Cl.[7] .............................................. G09B 23/26
(52) U.S. Cl. ........................ 434/278; 434/277; 434/281
(58) Field of Search ................................ 434/278, 279, 434/281, 282, 283, 298; 345/346, 348, 349, 355

(56) References Cited

U.S. PATENT DOCUMENTS

| | | | |
|---|---|---|---|
| 4,855,931 A | 8/1989 | Saunders | 364/499 |
| 5,249,137 A | * 9/1993 | Wilson et al. | 703/2 |
| 5,265,029 A | 11/1993 | Ramsay | 364/496 |
| 5,386,507 A | 1/1995 | Teig et al. | |
| 5,420,805 A | 5/1995 | Still et al. | 364/578 |
| 5,461,580 A | 10/1995 | Facci et al. | |
| 5,555,366 A | * 9/1996 | Teig et al. | 711/169 |
| 5,572,439 A | 11/1996 | Nishida et al. | |
| 5,742,290 A | 4/1998 | Hayano | 345/419 |
| 6,582,233 B1 | 6/2003 | Clark | 434/278 |

OTHER PUBLICATIONS

Zucker, "New for IBM and Mac: Drawing Program for Chemists", Newsbytes, Mar. 1991.*
Hanessian, et al., "Computer Assisted Analysis and Perception of Stereochemical Features in Organic Molecules Using the CHIRON Program", J. Chem. Inf. Comput. Sci., vol. 30, No. 4, (1990), pp. 413–425.
Seiter, "Alchemy II 1.01", Macworld, (1990), p 235.
Weininger, "Smiles. 3. Depict. Graphical Depiction of Chemical Structures", J. Chem. Inf. Comput. Sci., vol. 30, No. 3, (1990), pp. 237–242.
Cohen, "Drawing Package Knows Chemistry", MacWeek, vol. 5, No. 9, (1991) p. 12.
Zucker, "New for IBM and Mac: Drawing Program for Chemists", Newsbytes (1991).
Jenkins, Scott, Ph.D. "Drawn to Molecules: A Review of 2D Chemical Drawing Packages", Scitech Journal (1995), pp. 18–23.
Gonzalez–Platas et al., "Contour Maps Using the Bond–Valence–Sum Method", Journal of Applied Crystallography (1999) 32, pp. 341–344, XP–000956465, VALMAP2.0.

* cited by examiner

Primary Examiner—Kurt Fernstrom
(74) Attorney, Agent, or Firm—Knobbe Martens Olson & Bear LLP

(57) ABSTRACT

A computer implemented molecular modeler displays information concerning structural validity to the user. The display of information may be updated substantially continuously while the user modifies the molecular model. The display of information may comprise a color coded indicator and/or text associated with the atoms of the molecular model.

7 Claims, 9 Drawing Sheets

APPARATUS AND METHOD FOR MONITORING THE VALIDITY OF A MOLECULAR MODEL

CROSS REFERENCE OF RELATED APPLICATIONS

This application is a continuation of U.S. patent application Ser. No. 09/312,234 filed May 14, 1999 now U.S. Pat. No. 6,582,233.

BACKGROUND OF THE INVENTION

1. Field of the Invention

The invention relates to computer implemented molecular modeling tools and the display of molecular structures to a user.

2. Description of the Related Art

Chemists often find it desirable to visualize the structure of molecules in two or three dimensions. In rational drug design applications, for example, functional interactions between proteins and ligands can be illustrated by an analysis of the three dimensional structure of the two molecules. Protein-ligand binding sites, for example, may be discovered using such three dimensional models. Although such models were originally done with physical ball-and-stick or space filling kits, computer programs and high resolution graphic displays have become regularly used for the visualization of multidimensional molecular models. With these programs, a chemist can input a selected set of atoms and their bonds, thereby defining a molecular structure for display and analysis.

Originally, these computer programs were used mainly by highly trained computational chemists that specialized in the use of computer models to understand and predict chemical behavior. Over the past several years, however, bench chemists, biologists, and other researchers that work predominantly in the wet laboratory environment have begun to utilize computer modeling techniques to a much greater extent. This development has spurred the need to provide molecular modeling tools which are more user friendly than those previously available in the past.

In some currently available computer modeling programs, the physical validity of a molecular structure is evaluated automatically. It is well known to those in the art that one important aspect of the physical validity of a given molecular model is the satisfaction of the valences for each atom of the molecule. For example, the orbital configuration of the four valence shell electrons in carbon define a set of covalent bond structures for this element. Each of these configurations requires a total of four bonds between a given carbon and its covalently bonded partners to satisfy the valence of a given carbon atom. Similar considerations are present for other elements. Oxygen, for example requires two bonds for valence satisfaction.

With validity checking features as part of a molecular modeling program, the user may receive information from the program indicating whether or not a given atom has under or over filled valences. This feature may take a number of forms. In some programs, the user may select an atom, and a text window is displayed which includes an indication of the atom's valence status. If desired, the user may then close the text window and return to the molecular design algorithm to correct any problems set forth therein.

In a program commercially available under the name ISIS Draw™, from MDL Information Systems Inc., the user is informed when an over valence condition is about to be created during the process of designing the molecular structure. The user is then given the option to either refrain from placing the bond which will create the over valence condition, or to disable the validity checking from that atom. In the latter case, no further warnings are delivered to the user if additional bonds are made to the already over hybridized atom. ISIS Draw™ can also check the structure with a separate subroutine after the drawing is complete. This subroutine informs the user of problems, but does not identify the invalid atoms.

In a web-based program called Test Grins, available from Daylight Chemical Information Systems, Inc., the user first types a desired structure, and then runs a separate subroutine which checks the structure for over and under valenced atoms. The user may then return to the molecular design algorithm, and correct the problem atoms and/or bonds if desired.

In another program called CS ChemDraw, available from CambridgeSoft, the user can check the structure with a separate subroutine after the drawing is complete. This subroutine indicates problems with the molecular structure by highlighting one atom at a time.

In each of these cases, the information provided to the user is in a format which is relatively difficult to access and use, and in some cases does not indicate the portion of the molecular structure that is incorrect. Instant availability of information relating to the validity status of the atoms of a molecule being designed is not provided. There is therefore a need in the art to present this information to chemists performing computer implemented molecular modeling in a more user friendly format.

SUMMARY OF THE INVENTION

In one embodiment, the invention comprises a method of modeling molecular structure comprising the display of information representative of the physical invalidity of a modeled molecular structure and simultaneously accepting commands from a user to modify the modeled molecular structure.

The invention also comprises apparatus molecular modeling. In one embodiment, such apparatus comprises a display device for outputting a multidimensional representation of a user-defined molecular structure and an input device for receiving user commands to modify the user defined molecular structure. The apparatus further comprises a structure monitor comprising a plurality of validity attributes associated with a respective plurality of atoms of the user-defined molecular structure. The structure monitor is coupled to the display device so as to display information representative of a current status of the plurality of validity attributes. The structure monitor is coupled to the input device such that the current status is modified in response to user commands to modify the molecular structure. Thus, the display of information is updated as the molecular structure is modified by a user.

Another aspect of the invention comprises a computer readable media having instructions stored thereon which configure a general purpose computer to perform a method of molecular modeling comprising the simultaneous performance of (1) displaying information representative of physical invalidity of a molecular model and (2) accepting commands from a user to modify the molecular model.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable qualities or which is essential to practicing the inventions herein described.

Figure 1:
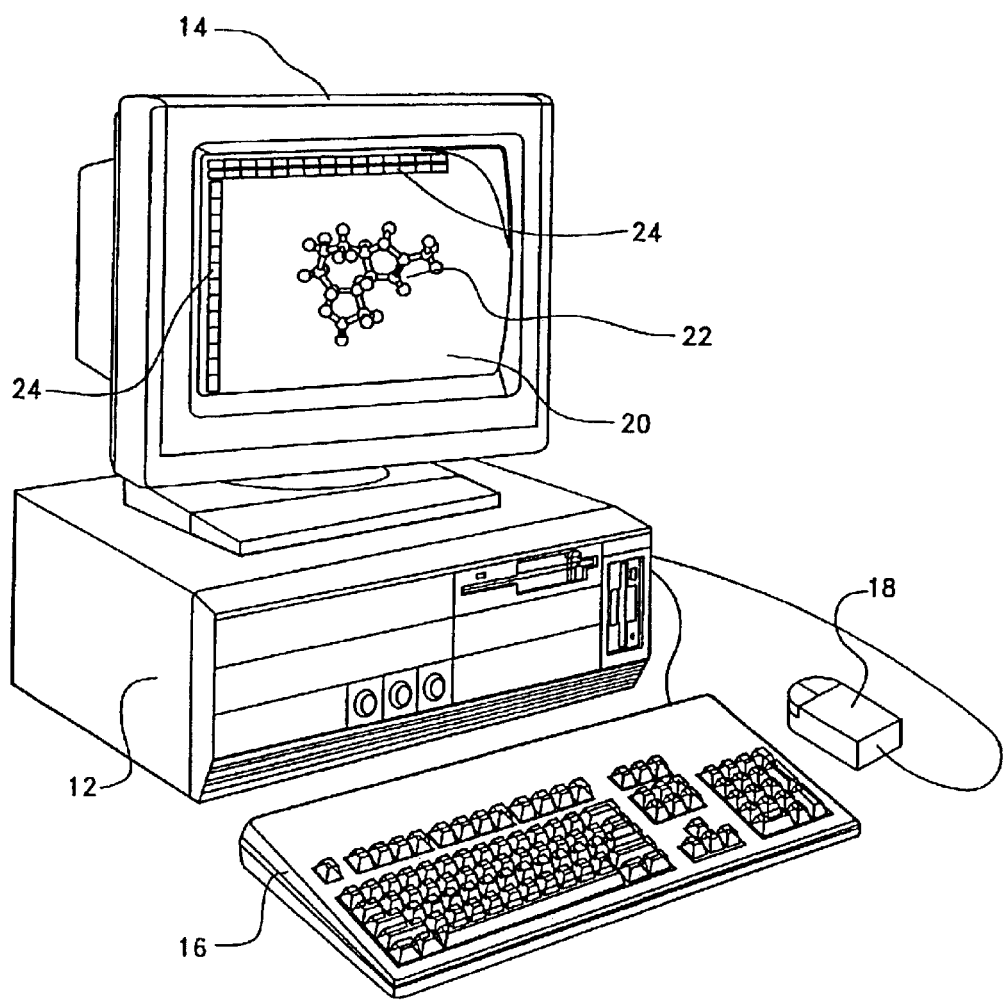
FIG. 1 is a perspective view of the computer environment the molecular modeler of the invention.

Referring now to FIG. 1, the molecular modelers of the invention comprise software code which configures a general purpose computer to display multi-dimensional models of user defined molecular structures. The code is typically provided to a user on a computer readable medium such as a CD-ROM or floppy disk. Once installed on a computer, the code is generally stored on a hard disk drive in the user's computer system. The nature of the computer may vary widely, and may include mainframes, mini-computer workstations, or personal microcomputers. As illustrated in FIG. 1, the host computer system comprises data processing hardware 12 including a computer readable memory such as semiconductor RAM and a hard disk drive for storing the code, as well as an associated display 14. The host system also typically includes input devices such as a keyboard 16 and mouse 18 for accepting user commands. It will be understood that the host hardware is conventional in nature and will not be described in further detail.

Also illustrated in FIG. 1 is a user interface 20 which is output on the display 14. This interface includes a region containing a display of a user-defined molecule 22, and may also include toolbars 24 defining user commands allowing modification and manipulation of the displayed molecule 22. User modification of a molecule may include the ability to add and delete atoms from the molecule, to change an atom from one element to another, or to alter bonds from, for example, a single bond to a double bond. The user may also be able to rotate or otherwise manipulate the display of the model. A wide variety of alternatives for the mouse and keyboard implemented alteration and manipulation of molecular model displays are known in the art, and may advantageously be used in conjunction with the invention described herein. One specific example for the task of drawing two dimensional molecular structures is described in U.S. Pat. No. 5,461,580 to Facci, et al., the disclosure of which is hereby incorporated by reference in its entirety.

Figure 2:
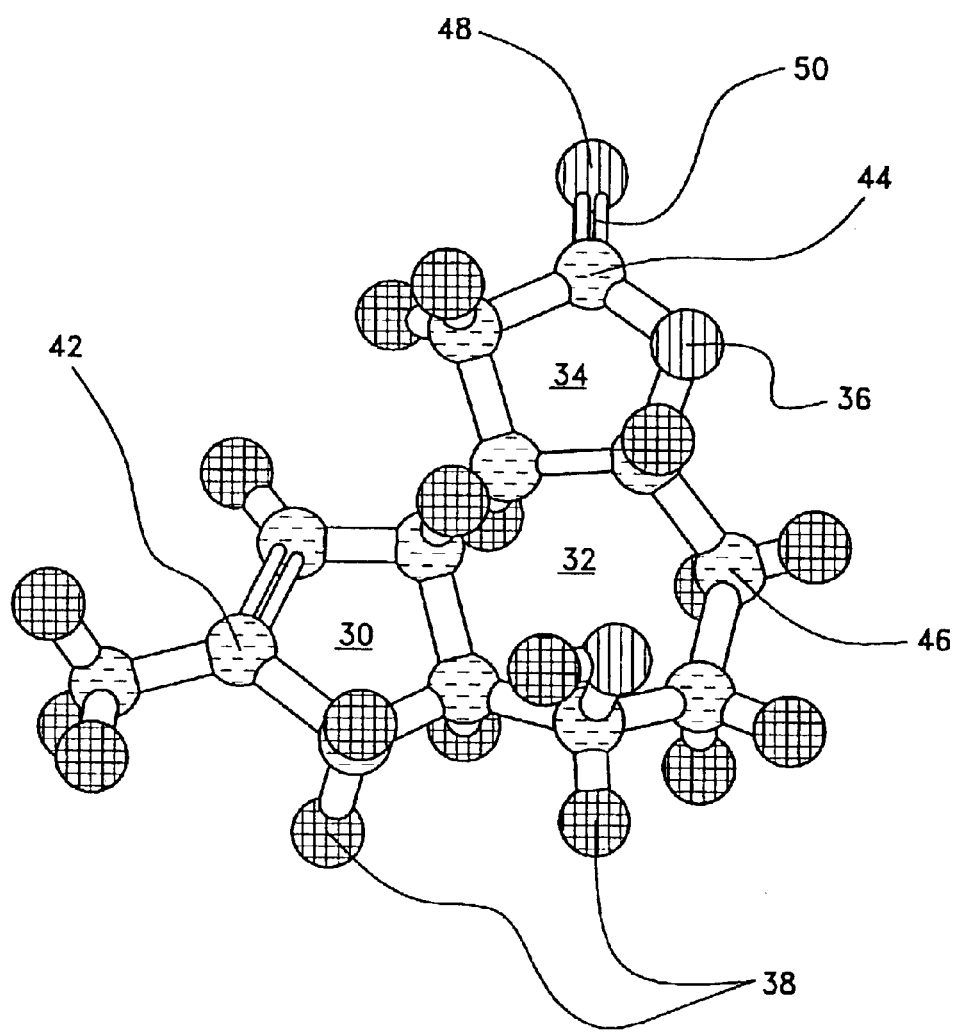
FIG. 2 is a screen display of a molecular model comprising atoms having properly filled valence shells.

FIG. 2 is an example screen display of a physically valid molecular model which may be displayed by a molecular modeling program in accordance with the invention. The display is in three-dimensional "ball and stick" format, and includes three joined ring structures. Two of the three ring structures 30, 32 are formed entirely from carbon atoms, and one of the rings 34 includes an oxygen atom 36. In the display embodiment of FIG. 2, oxygen atoms are indicated by different cross hatching styles. Hydrogen atoms 38 are indicated by a third different cross hatching style than both oxygen atoms and carbon atoms. In many advantageous embodiments of computer based molecular modeling programs, the different elements are color coded. For example, carbon may be displayed as gray, oxygen as red, and hydrogen as yellow. Other elements such as nitrogen, sulfur, etc. may be indicated by additional colors. The different cross hatching of FIG. 2 indicates this different perceived coloring to a user of the program. For clarity, this cross hatching for color indication is omitted from FIGS. 6, 7 and 8.

The molecular structure set forth in FIG. 2 has satisfied valences for all atoms in the structure. Of particular interest in the discussion below are the two $sp^2$ hybridized carbon atoms 42, 44, and the $sp^3$ hybridized carbon atom 46. It may also be noted that the oxygen atom 48 has a properly-satisfied valence via the double bond 50 between it and the covalently bound carbon atom 44.

Figure 3:
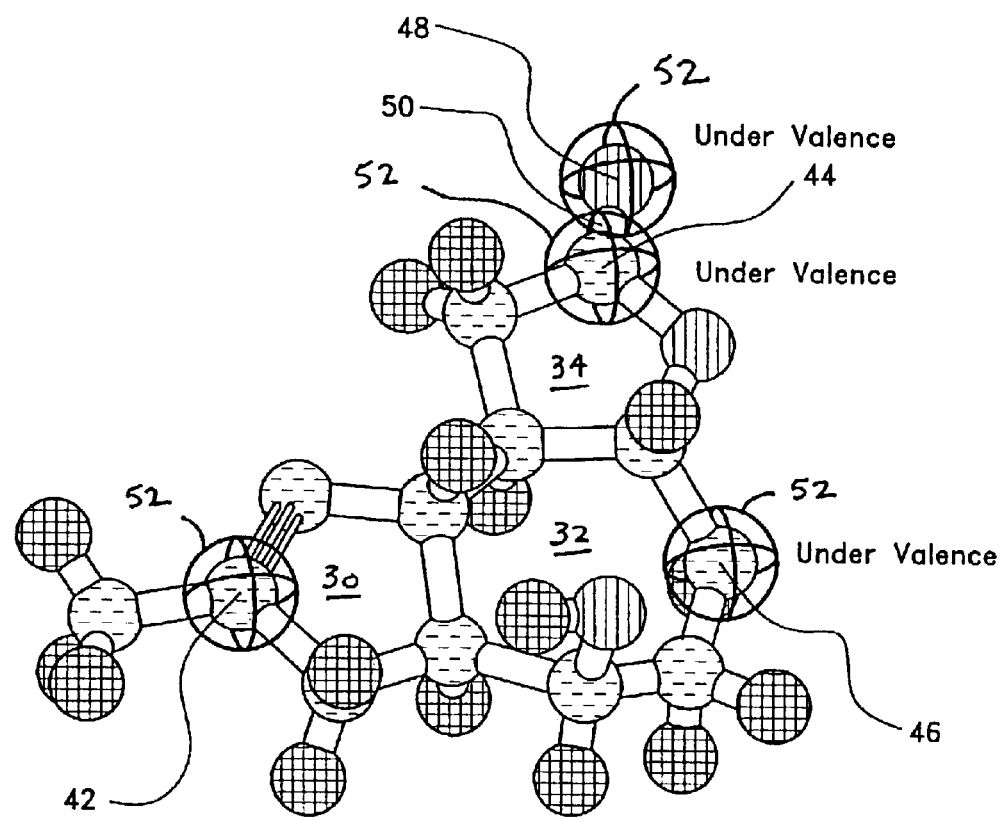
FIG. 3 is a screen display of a molecular model wherein valences for some atoms are improperly filled.

In FIG. 3, the molecular model of FIG. 2 has been modified to include improperly valenced atoms. In FIG. 3, the carbon atom 42 has been triple bonded to an adjacent carbon in the ring 30, rather than double bonded as shown in FIG. 2. This carbon atom 42 is now has over-filled valences, having five covalent bonds to neighboring atoms. In addition, the bond 50 between carbon atom 44 and oxygen atom 48 has been changed from a double bond to a single bond. This results in both the carbon atom 44 and the oxygen atom 48 having un-filled valences. Another modification is the removal of a hydrogen from carbon atom 46 of FIG. 2. Thus, this carbon atom 46 now has un-filled valences.

As can be seen in FIG. 3, the status of each of these atoms as improperly valenced is displayed in association with the relevant atom. In the embodiment illustrated in FIG. 3, one displayed feature which indicates the improperly valenced atoms is a surrounding "cage" 52. This cage 52 may be a different color depending on whether or not the atom has an under-filled or over-filled valence shell. For example, the cage around the over valenced atom 42 may be red, and the cage around the under-valenced atoms 44, 46, 48 may be yellow. A textual explanation of the valence problem may also be provided. In the embodiment of FIG. 3, for example, the under valenced atoms are provided with a legend stating "Under valence".

Figure 4:
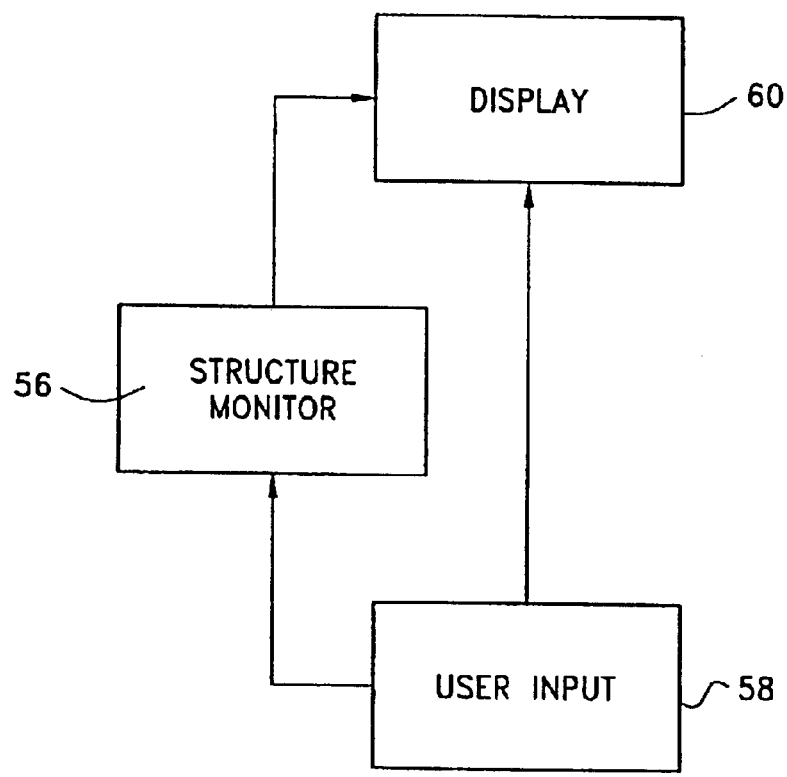
FIG. 4 is a block diagram of a portion of the components of the molecular modeler of the invention.

Advantageously, these displayed features which indicate the physical invalidity of a portion of a molecular model are updated and displayed substantially continuously as modifications to the molecular model are made by the user. Referring now to FIG. 4, this updating is accomplished by a structure monitor 56 provided as part of the modeling program. The structure monitor 56 comprises one or more validity attributes respectively associated with one or more of the atoms of the modeled molecule. In some advantageous embodiments, all atoms are assigned an associated validity attribute, although in some cases only a selected subset of atoms may have associated validity attributes. These validity attributes associated with the atoms track the physical validity status of the atoms of the molecular model.

The structure monitor 56 is coupled to both the user input 58, and the display 60. As the user modifies the molecular model with user input 58, both the validity attributes of the structure monitor 56 and the display 60 of the molecule itself are modified. Furthermore, the updated content of the validity attributes is sent to the display 60 such that these features, associated with the atoms, which indicate any physical invalidities are substantially continuously updated along with the display of the molecule.

Figure 5:
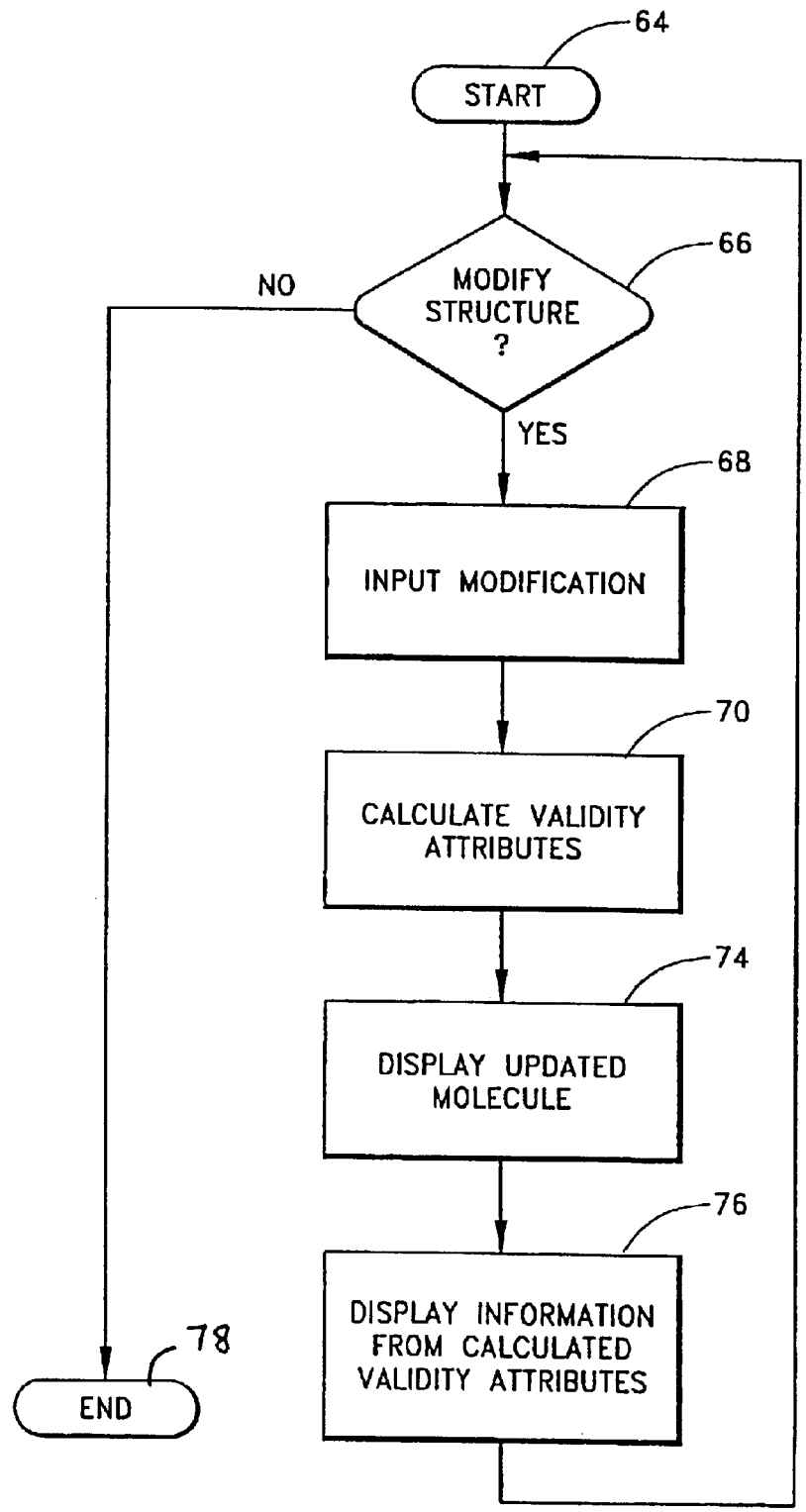
FIG. 5 is a flow chart of a process of updating a display of a molecular model in one embodiment of the invention.

FIG. 5 is a flowchart setting forth a method of updating a molecular display and an associated physical validity display in one embodiment of the invention. The method begins at a start state 64 and moves to a decision state 66 where the user decides whether to modify the structure of the molecular model. If modification is desired, at block 68 the user uses input devices such as the computer keyboard or mouse to define and enter the desired modification. The modification may comprise the addition or deletion of an atom or a group of atoms such as a ring or alkyl chain, the alteration of a bond between existing atoms, changing an atom from one element to another, etc. The modification may also comprise the creation of the first atom or multi-atom element of a new molecular structure being modeled. After the modification is input, validity attributes are calculated at block 70 for all or a selected set of the atoms of the modeled molecule. When a new atom is added to the model, a validity attribute associated with this new atom may be calculated. If the number of bonds is insufficient to fill the valence shell, the calculated validity attribute will indicate "under valence". Furthermore, the validity attribute associated with the atom to which the added atom is bonded may be re-calculated as "over valence", when prior to the modification it was calculated as properly valenced. Thus, each user defined change to the molecular model results in a recalculation of validity attributes for some or all of the atoms of the model.

At block 74, the molecular model is displayed with the modifications made by the user. At block 78, the updated status of the validity attributes for the atoms of the molecule are also displayed. Therefore, the user is provided with substantially constant feedback regarding the physical validity of the molecular model being analyzed. Preferably, the updating of the molecular display and the updating of the displayed invalidity information occurs substantially simultaneously for the user of the modeling program. That is, the displayed information concerning invalidities is modified continually while the user is viewing and modifying the molecular model. Validity checking thereby becomes a more interactive and useful tool for chemists using computer implemented molecular modeling. Users may, for example, view invalidity information associated with an atom of a molecular model, and simultaneously enter a modification to a bond so that the displayed invalidity information is altered. This alteration may comprise the elimination of the display indicating a physical invalidity. Thus, if the structure modification made by the user cures the valence problem, the display of may disappear as the modification is made. The user may therefore watch valence invalidities disappear in real time as the user modifies the molecule.

After the molecule and the displayed invalidity information is updated, the method of FIG. 5 loops back up to the decision block 66, where the user again determines whether to modify the molecular structure being modeled. If not, the method moves to end state 78. If additional modifications are desired, the process of updating the validity attributes and the display of the molecule and invalidity information is repeated as described above.

Figure 6:
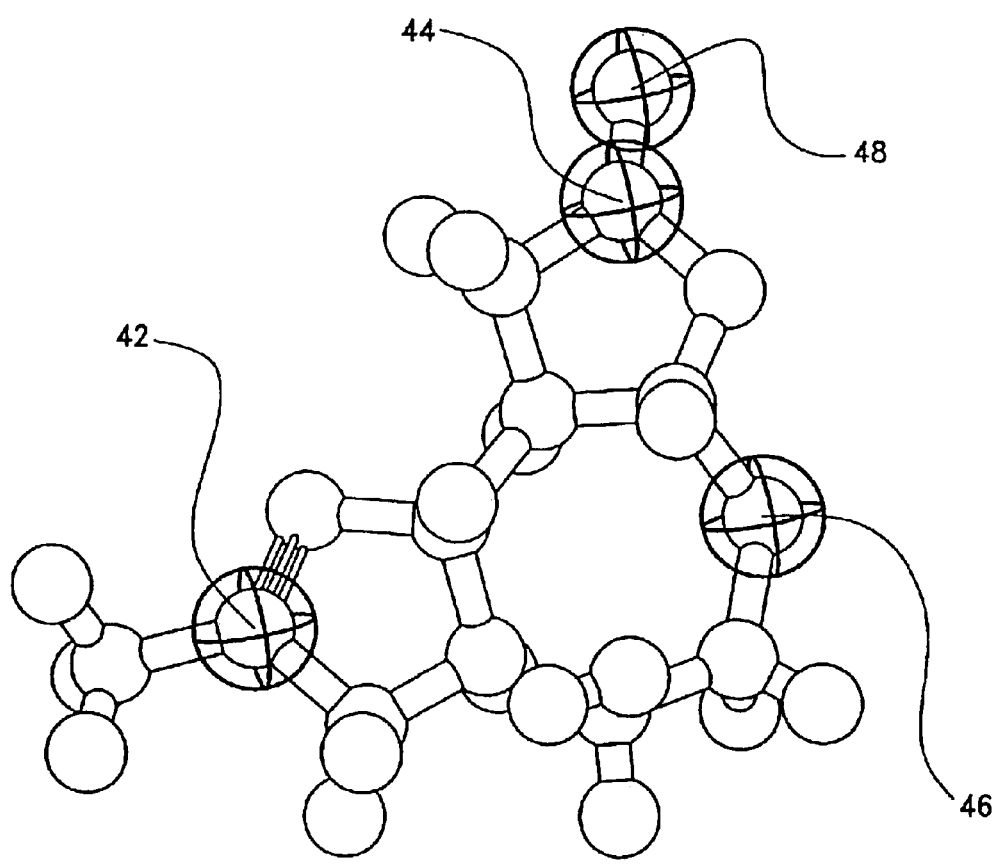
FIG. 6 is an alternative screen display of the structurally invalid molecular model of FIG. 3.
Figure 7:
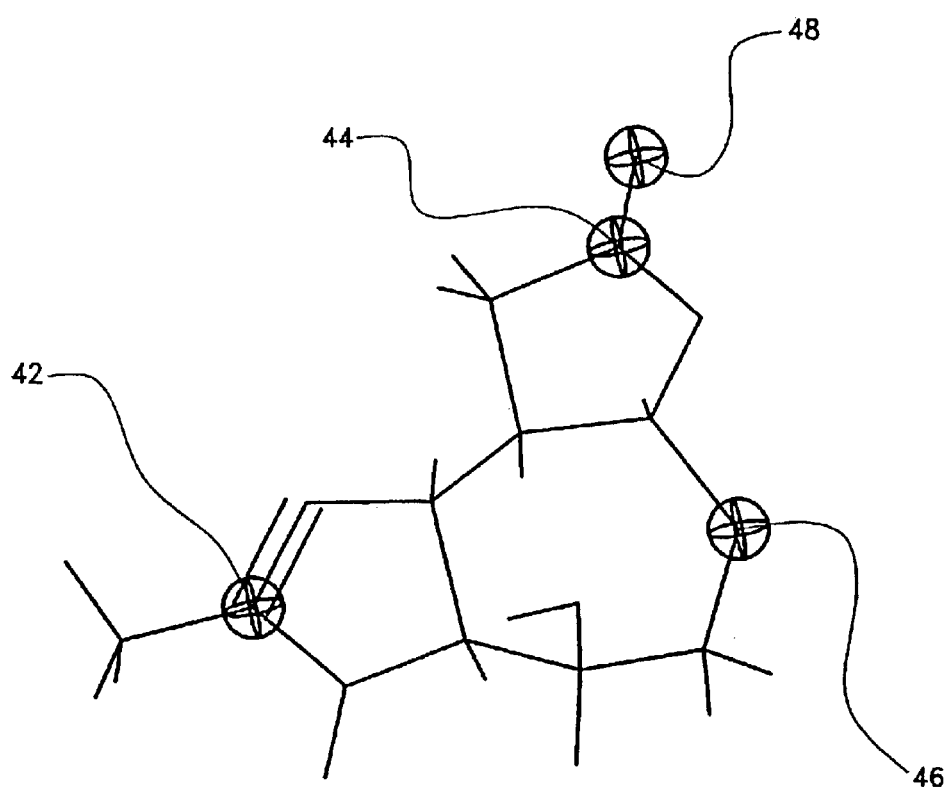
FIG. 7 is another alternative screen display of the structurally invalid molecular model of FIG. 3.
Figure 8:
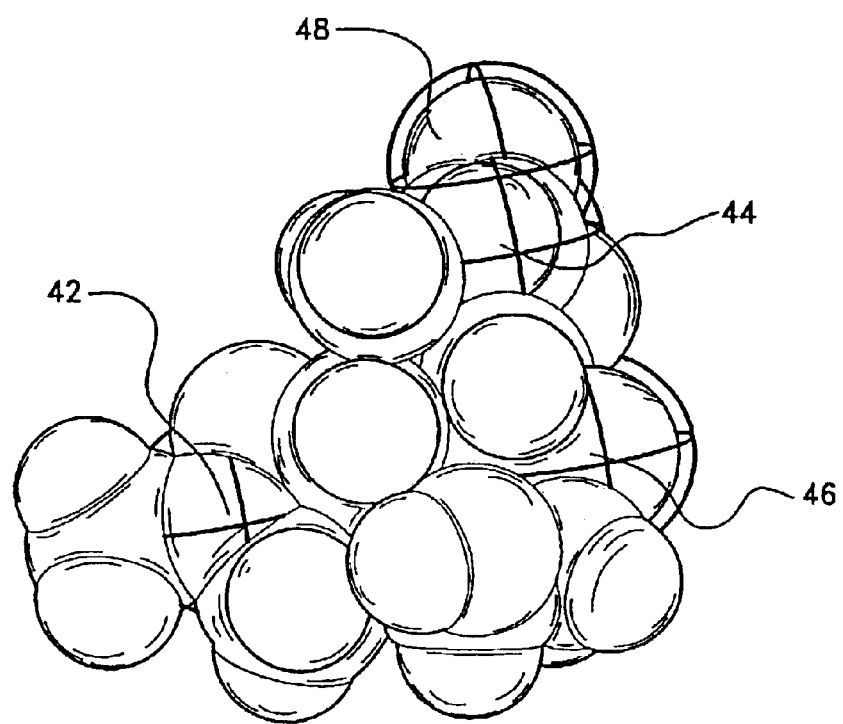
FIG. 8 is another alternative screen display of the structurally invalid molecular model of FIG. 3.

It will be appreciated that the invalidity information and the molecule can be displayed in many different formats. In FIG. 6, for example, the textual legend which appears in FIG. 3 is omitted. In FIG. 7, the molecule is presented in a "line" drawing rather than a ball and stick format. In this case, the colored cages surround endpoints of the lines where the relevant atoms reside. In FIG. 8, the colored cages surround the relevant atoms of a space filling representation of the modeled molecule of FIG. 3.

Figure 9:
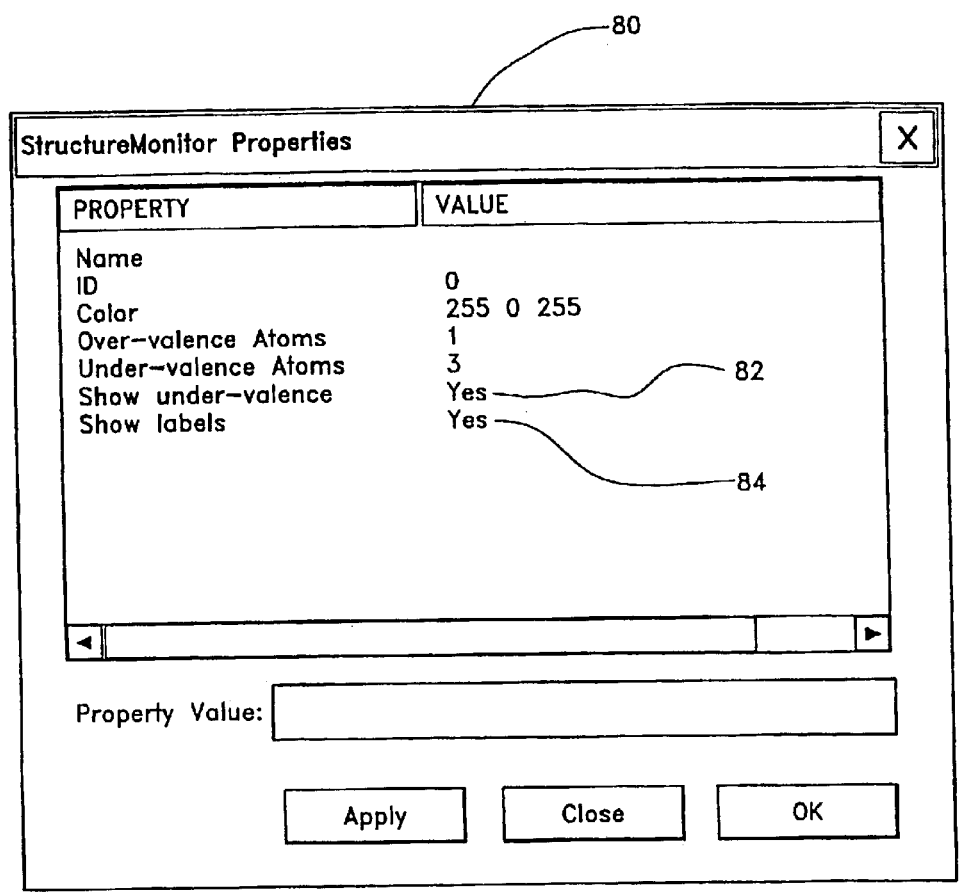
FIG. 9 is a screen display of a dialog box utilized by a user of one embodiment of the molecular modeler to modify the display of validity information.

In one advantageous embodiment of the invention, the nature of the display of invalidity information is user configurable. In this embodiment, the user may define the features which are displayed in association with the atoms of the molecule to indicate physical invalidity. FIG. 9 illustrates one implementation of this feature. This Figure illustrates a dialog box 80 that is user accessible. It may be user accessible through one of the toolbars 24 of FIG. 1 for example. This dialog box 80 sets forth at least some of the properties of the structure monitor 56 of FIG. 4. In the embodiment of FIG. 9, the user has a yes/no toggle 82 for selecting whether or not under valenced atoms are indicated as invalid or are instead, for example, assumed to have their valence completed by adding hydrogen atoms. The user also has another yes/no toggle 84 in this dialog box 80 for determining whether a textual explanation is provided for the valence problem. Thus, in some advantageous embodiments of the invention, the user may control what validity problems are displayed and/or how those problems are indicated. The dialog box may also indicate the total number of improperly valenced atoms. In the embodiment of FIG. 9, the number of under-valenced and over-valenced atoms are separately set forth.

It will be appreciated that a wide variety of implementations of the above described invention are possible while retaining its advantageous user interactive features. In this discussion, the proper valence status of the atoms of the molecule is the focus of the molecular validity analysis. However, those of skill in the art will recognize that validity attributes could also be associated with individual bonds of the structure, and may, for example, indicate to a user if a bond is too short or too long. Similar substantially continuously updated invalidity information could be provided for bond angles, non-bonded interatomic distances, as well as a variety of other parameters. In addition, the user may be provided with a wide variety of options for which types of information is displayed and the format it is displayed in. In some advantageous embodiments, the user may be allowed to choose different display options for different atoms and bonds.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of modeling a molecular structure comprising:

providing a user with a plurality of options for different display formats for a validity attribute of at least one atom of said molecular structure;

receiving a selection of at least one of said plurality of options from said user;

assigning said validity attribute to said at least one atom of said molecular structure; and displaying at least a portion of the content of said validity attribute in said selected display format.

2. The method of claim 1, wherein said displaying a feature comprises displaying text.

3. The method of claim 1, wherein said displaying a feature comprises displaying a user defined color associated with said atom.

4. The method of claim 3, wherein said displaying a feature comprises displaying text.

5. The method of claim 1, additionally comprising assigning a validity attribute to at least one bond of said molecular structure.

6. The method of claim 1, wherein said validity attribute comprises information indicating whether said atom comprises under-filled or over-filled valence shells.

7. A method of modeling molecular structure, comprising:

displaying a user modifiable molecular structure;

while the molecular model is being displayed and modified by the user, calculating validity attributes for a plurality of atoms or bonds in said molecular model as the user performs a modification to said molecular model, said plurality comprising at least one atom or bond not modified by said modification; and while the molecular model is being displayed and modified by the user, providing the user with automatic and substantially continuous displayed feedback regarding the physical validity of said plurality of atoms or bonds as the user performs said modification, wherein said modification modifies only an individual atom or bond of the molecular structure.

* * * * *